United States Patent
Punjani

(10) Patent No.: US 11,977,039 B2
(45) Date of Patent: May 7, 2024

(54) METHODS AND SYSTEMS FOR DETERMINING VARIABILITY OF CRYO-EM PROTEIN STRUCTURES

(71) Applicant: STRUCTURA BIOTECHNOLOGY INC., Toronto (CA)

(72) Inventor: Ali Punjani, Toronto (CA)

(*) Notice: Subject to any disclaimer, the term of this patent is extended or adjusted under 35 U.S.C. 154(b) by 359 days.

(21) Appl. No.: 17/617,076

(22) PCT Filed: Jun. 5, 2020

(86) PCT No.: PCT/CA2020/050775
§ 371 (c)(1),
(2) Date: Dec. 7, 2021

(87) PCT Pub. No.: WO2020/243839
PCT Pub. Date: Dec. 10, 2020

(65) Prior Publication Data
US 2022/0236201 A1    Jul. 28, 2022

Related U.S. Application Data

(60) Provisional application No. 63/006,385, filed on Apr. 7, 2020, provisional application No. 62/858,430, filed on Jun. 7, 2019.

(51) Int. Cl.
*G01N 23/2252* (2018.01)
*G16B 15/20* (2019.01)

(52) U.S. Cl.
CPC ......... *G01N 23/2252* (2013.01); *G16B 15/20* (2019.02); *G01N 2223/401* (2013.01); *G01N 2223/418* (2013.01); *G01N 2223/612* (2013.01)

(58) Field of Classification Search
CPC ........... G01N 23/2252; G01N 23/2251; G01N 2223/401; G01N 2223/418; G01N 2223/612; G16B 15/20; G06F 17/16
(Continued)

(56) References Cited

U.S. PATENT DOCUMENTS

2020/0333270 A1* 10/2020 Punjani .................. G06T 17/00
2022/0002701 A1*  1/2022 Chen ................ G01N 33/56983

FOREIGN PATENT DOCUMENTS

CA    3078256 A1    4/2019

OTHER PUBLICATIONS

Extended European search report for European application No. 20818111.5, EPO, dated May 3, 2023.
(Continued)

*Primary Examiner* — Kiet T Nguyen
(74) *Attorney, Agent, or Firm* — Bhole IP Law; Anil Bhole; Marc Lampert

(57) ABSTRACT

There is provided systems and methods for determining variability of cryo-EM protein structures from a set of cryo-electron microscope images. The method includes: performing iterative optimization, each optimization iteration including: determining the updated variability coordinates for individual images from the set of images using a current value of the variability components; determining the updated variability components for multiple images of the set of images, using the updated value of the variability coordinates, by solving a set of linear equations, the linear equations comprising a sum of weighted compositions of projection and back-projection operators, the equations are solved by arranging the equations into a block-diagonal matrix form.

20 Claims, 11 Drawing Sheets

(58) Field of Classification Search
USPC .......................................................... 250/310
See application file for complete search history.

(56) References Cited

OTHER PUBLICATIONS

International Search Report for PCT application No. PCT/CA2020/050775, search completed: Aug. 7, 2020, dated Aug. 26, 2020.
Third Party Observation Report for PCT application No. PCT/CA2020/050775, dated Jan. 14, 2021.
Written Opinion of the International Searching Authority for PCT application No. PCT/CA2020/050775, CIPO, opinion completed: Aug. 14, 2020, dated Aug. 26, 2020.
Anden, Joakim, et al., "Covariance estimation using conjugate gradient for 3D classification in Cryo-EM", 2015 IEEE 12th International Symposium on Biomedical Imaging (ISBI). https://doi.org/10.1109/isbi.2015.7163849, Apr. 16, 2015.
Anden, Joakim, et al., "Structural Variability from Noisy Tomographic Projections", (2018). SIAM Journal on Imaging Sciences, 11(2), 1441-1492. https://doi.org/10.1137/17m1153509, May 31, 2018.
Jacob, Mathews, et al., "3-D Shape Estimation of DNA Molecules From Stereo Cryo-Electron 1-24 Micro-Graphs Using a Projection-Steerable Snake", IEEE Transactions on Image Processing, vol. 15, No. 1, Jan. 1, 2006 (Jan. 1, 2006), pp. 214-227, XP055766552, USA, ISSN: 1057-7149, DOI: 10.1109/TIP.2005.860310, Jan. 1, 2006.
Jonić, Slavica, "Computational methods for analyzing conformational variability of macromolecular complexes from cryo-electron microscopy images", (2017) Current Opinion in Structural Biology, 43, 114-121. https://doi.org/10.1016/j.sbi.2016.12.011, 2017.
Lederman, Roy R., et al., "Continuously heterogeneous hyper-objects in cryo-EM and 3-D movies of many temporal dimensions", (2017). Arxiv., 2017.
Nakane, Takanori, et al., "Characterisation of molecular motions in cryo-EM single-particle data by multi-body refinement in RELION", (2018) ELife, 7. https://doi.org/10.7554/elife.36861, Jun. 1, 2018.
Penczek, Pawel A., et al., "Identifying conformational states of macromolecules by Eigen-analysis of resampled cryo-EM images", (2011). Structure, 19(11), 1582-1590. https://doi.org/10.1016/j.str.2011.10.003, 2011.
Riasati, Vahid R., et al., "Pressing the sparsity advantage via data-based decomposition", Proceedings of SPIE, IEEE, USA, vol. 9460, May 19, 2015 (May 19, 2015), pp. 94600J-1-94600J-16, XP060054994, DOI: 10.1117/12.2177290, ISBN: 978-1-62841-730-2.
Scheres, S.H.W., "Processing of structurally heterogeneous cryo-EM data in RELION", (2016). Methods in Enzymology, 125-157. https://doi.org/10.1016/bs.mie.2016.04.012, 2016.
Tagare, Hemant D., et al., "Directly reconstructing principal components of heterogeneous particles from cryo-EM images", (2015) Journal of Structural Biology, 191(2), 245-262. https://doi.org/10.1016/j.jsb.2015.05.007, Aug. 1, 2015.
Xu, Nan, et al., "Reconstruction of Stochastic 3D Signals With Symmetric Statistics From 2D Projection Images Motivated by Cryo-Electron Microscopy", IEEE Transactions on Image Processing, IEEE, USA, vol. 28, No. 11, May 14, 2019 (May 14, 2019), pp. 5479-5494, XP011741864, ISSN: 1057-7149, DOI: 10.1109/TIP.2019.2915631.

* cited by examiner

METHODS AND SYSTEMS FOR DETERMINING VARIABILITY OF CRYO-EM PROTEIN STRUCTURES

TECHNICAL FIELD

The following relates generally to electron Cryo-microscopy; and more specifically, to systems and methods for determining variability of cryo-EM protein structures.

BACKGROUND

Proteins are the molecular machines of life. 3D protein structures inside and outside the cell carry out all functions of all known living organism. The essential characteristic of functional proteins is that they perform actions at the molecular scale by literally acting as mechanical machines, with bending, turning, swiveling, ratcheting, sliding, and other motions of their parts in order to cause the operands on which they operate to be arranged and transformed in a particular way. Proteins also change not only with moving parts, but also with mechanisms such as association and dissociation of subunits during particular functions. All these types of variation in the 3D structure of a protein mean that any individual protein molecule of a certain type may be found in a multitude of possible heterogeneous states.

In Electron Cryo-microscopy (also referred to as Cryo-electron microscopy or "cryo-EM"), many protein molecules (thousands to millions, for example) of ideally the same type are purified biochemically, and then prepared into a frozen sample. In this sample, the protein molecules (each called a particle) are all facing in different directions (i.e. having different 3D poses) and also may be in different states in terms of their variability (moving parts, flexible parts, rotating subunits, association/dissociation). Ideally, the set of all individual single particles in the sample are a representative population, covering all the possible states that the protein can assume. The individual particles are imaged in an electron microscope and together these individual particle images are used computationally to reconstruct a 3D structure (in the form of a 3D electron density map) of the target protein.

SUMMARY

In an aspect, there is provided a method for determining variability of cryo-EM protein structures from a set of cryo-electron microscope images, the variability represented as a model comprising variability components in a weighted sum, the weights in the weighted sum comprising variability coordinates for each component for each image, the method comprising: receiving the set of images; performing iterative optimization to determine updated variability components and updated variability coordinates for the received set of images, each optimization iteration comprising: determining the updated variability coordinates for individual images from the set of images using a current value of the variability components; and determining the updated variability components for multiple images of the set of images, using the updated value of the variability coordinates, by solving a set of linear equations, the linear equations comprising a sum of weighted compositions of projection and back-projection operators, the equations are solved by arranging the equations into a block-diagonal matrix form; and outputting the variability components.

In a particular case of the method, determining the updated variability coordinates comprises solving a linear system, the linear system comprising inner-products between projections from multiple variability components and inner-products between image data of the set of images and variability components.

In another case of the method, the optimization iteration further comprising determining a per-particle contrast scale factor, the per-particle contrast scale factor is multiplied on the weighted sum of variability components in the model.

In yet another case of the method, the block-diagonal form is solved by separating the block-diagonal into independent sub matrices.

In yet another case of the method, iterations are initialized with a random initial value for the unknown variability coordinates.

In yet another case of the method, the iterations are performed a predetermined number of times.

In yet another case of the method, the iterations are performed until convergence is detected based on a change in values for variability between successive iterations.

In yet another case of the method, the method further comprising performing orthogonalization of the variability components after solving the set of linear equations.

In yet another case of the method, the orthogonalization of the variability components comprises determining a cross-correlation matrix of the variability components, diagonalizing the cross-correlation matrix using eigendecomposition, and using a resulting rotation matrix on density vectors of the variability components to become orthogonal.

In yet another case of the method, the orthogonalization of the variability components comprises performing Gram-Schmidt orthogonalization.

In yet another case of the method, the method further comprising clustering the set of images into separate subsets associated with different conformations of the protein structure using the optimized variability coordinate values as input.

In yet another case of the method, the method further comprising performing the iterative optimization on the subsets of images, and further comprising performing clustering of the optimized variability coordinate values on the subsets of images.

In another aspect, there is provided a system for determining variability of cryo-EM protein structures from a set of cryo-electron microscope images, the variability represented as a model comprising variability components in a weighted sum, the weights in the weighted sum comprising variability coordinates for each component for each image, the system comprising one or more processors in communication with a memory storage, the one or more processors configured to execute: an inputs module to receive the set of images; an optimization module to perform iterative optimization to determine updated variability components and updated variability coordinates for the received set of images, each optimization iteration comprising: determining the updated variability coordinates for individual images from the set of images using a current value of the variability components; and determining the updated variability components for multiple images of the set of images, using the updated value of the variability components, by solving a set of linear equations, the linear equations comprising a sum of weighted compositions of projection and back-projection operators, the equations are solved by arranging the equations into a block-diagonal matrix form; and an output module to output the variability components.

In a particular case of the system, determining the updated variability coordinates comprises solving a linear system, the linear system comprising inner-products between projections from multiple variability components and inner-products between image data of the set of images and variability components.

In another case of the system, the optimization iteration further comprising determining a per-particle contrast scale factor, the per-particle contrast scale factor is multiplied on the weighted sum of variability components in the model In yet another case of the system, the block-diagonal form is solved by separating the block-diagonal into independent sub matrices.

In yet another case of the system, each iteration comprises a random initial value for the unknown coordinates.

In yet another case of the system, iterations are initialized with a random initial value for the unknown variability coordinates.

In yet another case of the system, the iterations are performed until convergence is detected based on a change in values for variability between successive iterations.

In yet another case of the system, the optimization module further performs orthogonalization of the variability components after solving for the set of linear equations.

In yet another case of the system, the orthogonalization of the variability components comprises determining a cross-correlation matrix of the variability components, diagonalizing the cross-correlation matrix using eigendecomposition, and using a resulting rotation matrix on density vectors of the variability components to become orthogonal.

In yet another case of the system, determining the orthogonalization of the variability components comprises performing Gram-Schmidt orthogonalization.

In yet another case of the system, the optimization module further clusters the set of images into separate subsets associated with different conformations of the protein structure using the optimized variability coordinate values as input.

In yet another case of the system, the optimization module further performs the iterative optimization on the subsets of images, and further performs clustering of the optimized variability coordinate values on the subsets of images These and other aspects are contemplated and described herein. It will be appreciated that the foregoing summary sets out representative aspects of systems and methods to assist skilled readers in understanding the following detailed description.

DESCRIPTION OF THE DRAWINGS

The features of the invention will become more apparent in the following detailed description in which reference is made to the appended drawings wherein.

DETAILED DESCRIPTION

Figure 1:
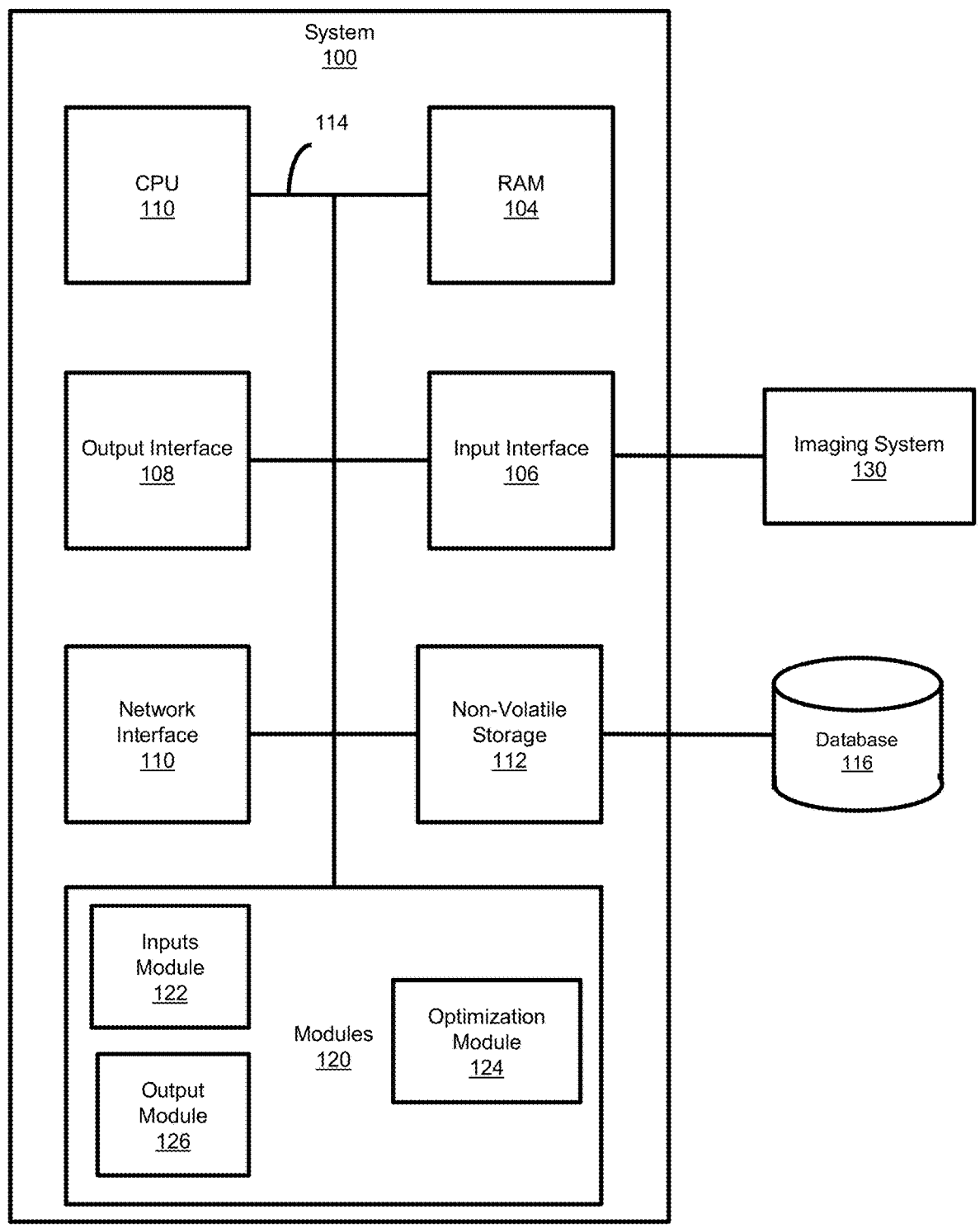
FIG. 1 shows a system for determining variability of cryo-EM protein structures, according to an embodiment.

For simplicity and clarity of illustration, where considered appropriate, reference numerals may be repeated among the Figures to indicate corresponding or analogous elements. In addition, numerous specific details are set forth in order to provide a thorough understanding of the embodiments described herein. However, it will be understood by those of ordinary skill in the art that the embodiments described herein may be practiced without these specific details. In other instances, well-known methods, procedures and components have not been described in detail so as not to obscure the embodiments described herein. Also, the description is not to be considered as limiting the scope of the embodiments described herein.

Various terms used throughout the present description may be read and understood as follows, unless the context indicates otherwise: "or" as used throughout is inclusive, as though written "and/or"; singular articles and pronouns as used throughout include their plural forms, and vice versa; similarly, gendered pronouns include their counterpart pronouns so that pronouns should not be understood as limiting anything described herein to use, implementation, performance, etc. by a single gender; "exemplary" should be understood as "illustrative" or "exemplifying" and not necessarily as "preferred" over other embodiments. Further definitions for terms may be set out herein; these may apply to prior and subsequent instances of those terms, as will be understood from a reading of the present description.

Any module, unit, component, server, computer, terminal, engine or device exemplified herein that executes instructions may include or otherwise have access to computer readable media such as storage media, computer storage media, or data storage devices (removable and/or non-removable) such as, for example, magnetic disks, optical disks, or tape. Computer storage media may include volatile and non-volatile, removable and non-removable media implemented in any method or technology for storage of information, such as computer readable instructions, data structures, program modules, or other data. Examples of computer storage media include RAM, ROM, EEPROM, flash memory or other memory technology, CD-ROM, digital versatile disks (DVD) or other optical storage, magnetic cassettes, magnetic tape, magnetic disk storage or other magnetic storage devices, or any other medium which can be used to store the desired information and which can be accessed by an application, module, or both. Any such computer storage media may be part of the device or accessible or connectable thereto. Further, unless the context clearly indicates otherwise, any processor or controller set out herein may be implemented as a singular processor or as a plurality of processors. The plurality of processors may be arrayed or distributed, and any processing function referred to herein may be carried out by one or by a plurality of processors, even though a single processor may be exemplified. Any method, application or module herein described may be implemented using computer readable/executable instructions that may be stored or otherwise held by such computer readable media and executed by the one or more processors.

Various techniques have used algorithmic and computational data processing that can isolate subsets of particles (classes) that are each in a different distinct 3D conformation (i.e., state of the molecule under study). These include 2D and 3D classification and various similar approaches. These techniques are able to solve a clustering problem, where the cluster centers represent the rigid 3D structure of each discrete state, and the assignment of particles into the clusters provides information about which particle came from which cluster.

Embodiments of the present disclosure provide a technological solution to a different technical problem, where the task is to deal with continuous heterogeneity. In this setting, there are a continuum of states which the particles take on, rather than multiple discrete states. The continuum generally cannot be well approximated by a single rigid structure, so the result of using the previous techniques on data of this sort is that flexible and dynamic regions of a molecule become blurred out and hazy.

Continuous heterogeneity generally occurs in almost all molecules-of-interest, since as mentioned, all molecules that have a function act via mechanical mechanisms that necessitate movement and flexibility for functional operation of a protein. Several attempts have been made to solve this problem, with multiple formulations of the problem and methods for computing a result. Embodiments of the present disclosure provide approaches for successfully determining multiple underlying components of the three-dimensional (3D) variability present in a set of images of protein particles. In various cases, these approaches could be used for both two-dimensional (2D) images (e.g., from single-particle Cryo-EM) or 3D images (e.g., from cryotomography).

Consider the setting where multiple 2D single particle images are observed, each denoted as a vector of pixel values $X_i$ where i ranges from 1 to N, the total number of images. The following describes the case of 2D images but is equally valid for 3D images X. Each image is an image of a single protein particle, and in a given image, the image is corrupted by a given microscope contrast transfer function $C_i$, the protein takes on a particular 3D pose $\phi_i$ (which could be represented in any parameterization, e.g., Euler angles or axis-angle coordinates) and also takes on a particular 3D state (i.e., conformation) of the protein. This 3D state can include, for example, flexibility, presence or absence of subunits, binding of a ligand, and the like. The 3D state can be described, for each image, with a vector $z_i$ of "variability coordinates". These coordinates (denoted $z_{ik}$ for the k'th coordinate of the i'th image), are each a number specifying the state of the protein in the ith image along each of K dimensions of variability that are being considered. This means that for the i'th image, the protein molecule itself can be described as a vector $V(z_i)$ of electron density values (or any other equivalent representation, for example, Fourier-space components describing the protein density). This vector V is a function of the coordinates z, and is a set of numbers that describes the 3D structure of the protein in terms of the amount of electron density at each point in the molecule; for example, on a discrete grid in 3D space. This is generally referred to as a 3D density map. Note that in a typical context, the images V and X will have a size of several hundred pixels or voxels in each dimension, and the number of images N will be in the hundreds of thousands or millions. In the present embodiments, these billions or trillions of values generally need to be considered simultaneously, and thus complex non-intuitive computational steps need to be applied for these values. These computational operations generally require the substantial task of holding vast arrays of numbers in memory simultaneously and performing aggregate operations on them. In this way, as described herein, the present embodiments advantageously provide a substantial advancement in the field of electron cryo-microscopy and the resulting structural biology it enables.

The present embodiments can be used in many applications, for example, discrete heterogeneity, continuous flexibility, the binding or release of ligands, association and dissociation of protein complexes, and the like. All types of variability within the dataset of images $X_i$ can be described in the setup of the problem.

Other approaches to the above problem include:
attempting to construct a non-linear manifold embedding to describe the variability of the molecule;
adding multiple assumptions about the form of the variability in the molecule, in order to be able to solve low resolution coarse approximations to the variability components; and
making use of mathematical and computational approximations, and thus providing only low-resolution results.

The above approaches can be grouped into two categories. First, is a category of approaches that consider a model of protein variability that is a linear model, meaning that it characterizes linear components of variability in the space of 3D structures. More concretely, the model above is written as a linear function: $V(z_i) = \Sigma_k z_{ik} V_k$ where each $V_k$ is one linear component of variability of the molecule, with k ranging from 1 to K. The second category consists of approaches that consider the variability to be non-linear, so that $V(z_i)$ is a non-linear function of some specified form. In contrast, the present embodiments provide an approach that falls into the first category, where the variability is considered to be linear. In this setting, the problem is briefly summarized as: given images $X_i$ (and optionally the poses $\phi_i$), find the components of variability $V_k$ and the coordinates for each image $z_i$.

It is notable that the above problem, of finding the $V_k$ and $z_i$ in a linear setting, may be considered similar to Principle Components Analysis (PCA); but there are multiple characteristics that make it impossible to apply PCA to this problem. First, PCA generally requires that all observations be complete, with no missing data. In the problem context of 3D variability above, each observation in fact has a large amount of missing data, given that each observation is only a 2D image of a 3D protein molecule. All information about the 3D structure is lost, and only a 2D projection is observed in each image. Second, PCA (and other similar approaches) are generally not formulated in a way that can handle the presence of the contrast transfer function (CTF) of the microscope, which can distort each observation in a different way. No single image $X_i$ is actually a true observation of the underlying protein electron density; instead, due to electron optics in the microscope, each observation $X_i$ is a CTF-corrupted observation, and the CTF is different in each image. Third, the standard PCA method requires forming a large sample covariance matrix of all observed data. The size of the matrix is equal to the number of voxels in a 3D density map squared, which for this problem would become intractably large and impossible to store even on the largest computers. In this way, it is effectively impossible to apply PCA without resorting to crude approximations.

In terms of nomenclature, the present embodiments provide approaches for estimating the covariance structure of a sample of data. In particular, the volume $V(z_i)$ can be thought of as a sample from a probability distribution. Each single particle image contains one such sample, and the combination of all images yields a multitude of samples. Finding a linear model to represent $V(z_i)$ is equivalent to finding the eigenvectors of the covariance matrix that describes the samples.

Embodiments of the present disclosure advantageously solve the above 3D variability task, without approximations, to enable the determination of multiple components of variability from a dataset, and each component of variability (as illustrated in the example experiments below) contains information about the nature of the protein molecule itself, in the form of biological insight into it's mechanical function, at high resolution. The resulting components $V_k$ and coordinates $z_i$ can also be used as the basis for several further approaches to further improve the resolution and insight that can be gained from the images $X_i$. Approaches of the present disclosure can use a set of computational steps in the context of 2D and 3D images of molecules to yield 2D or 3D reconstructions of the variability present in the images, and this capability directly advances the technology of electron cryo-microscopy by making it possible to determine and visualize the mechanical function of biological molecules, a capacity that previous technologies have generally not been able to deliver.

Referring now to FIG. 1, a system 100 for determining variability of cryo-EM protein structures, in accordance with an embodiment, is shown. The system 100 can be executed on a suitable computing device; for example, a desktop computer, a laptop computer, a server, or the like.

FIG. 1 shows various physical and logical components of an embodiment of the system 100. As shown, the system 100 has a number of physical and logical components, including a central processing unit ("CPU") 102, random access memory ("RAM") 104, an input interface 106, an output interface 108, a network interface 110, non-volatile storage 112, and a local bus 114 enabling CPU 102 to communicate with the other components. CPU 102 executes various modules 120, as described below in greater detail. RAM 104 provides relatively responsive volatile storage to CPU 102. The input interface 106 enables an administrator or user to provide input via an input device, for example a keyboard and mouse. The output interface 108 outputs information to output devices, such as a display and/or speakers. The network interface 110 permits communication with other systems, such as other computing devices and servers remotely located from the system 100, such as for a typical cloud-based access model. Non-volatile storage 112 stores computer-executable instructions for implementing the modules, as well as any data used by these services. Additional stored data can be stored in a database 116. During operation of the system 100, the modules and the related data may be retrieved from the non-volatile storage 112 and placed in RAM 104 to facilitate execution.

In an embodiment, as described in more detail in the following, the system 100 includes various modules 120; including an inputs module 122, an optimization module 124, and an output module 126. In further cases, the functions of some or all of the various modules 120 can be combined or performed on other modules, or can be performed on dedicated pieces of hardware. In some cases, some or all of the various modules 120 can be executed on a server-side device 32 or a client-side device 26 (shown in FIG. 2), and be in communication with the other modules.

An imaging system 130 may further be linked to the system 100 to obtain cryo-EM images. The imaging system 130 generally comprises one or more electron microscopes, or other suitable devices.

Figure 2:
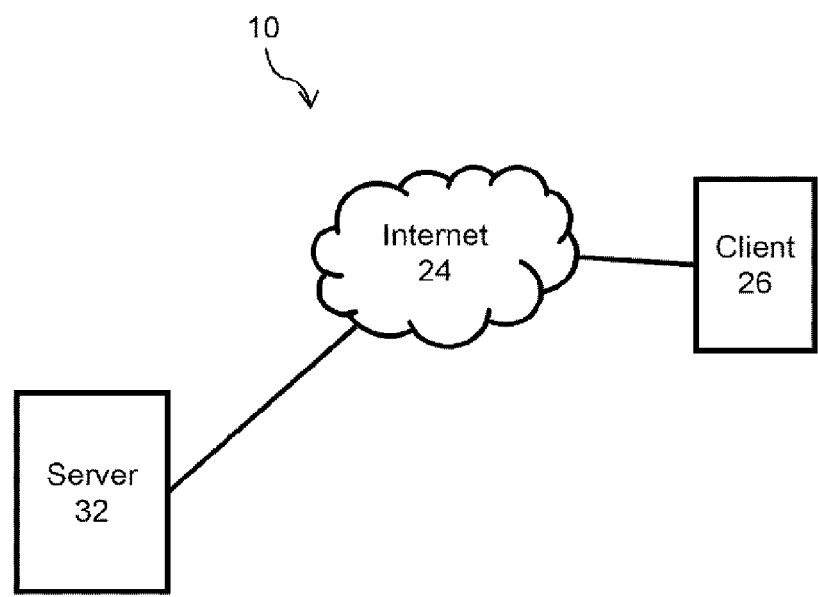
FIG. 2 shows a computing environment of the system of FIG. 1.

In some cases, as shown in a diagram of a computing environment 10 in FIG. 2, the system 100 can communicate with, and retrieve data, from other computing devices; for example, from the server 32 to the client computing device 26. The system 100 can communicate with these devices over a data communication network; for example, the Internet 24.

Figure 3:
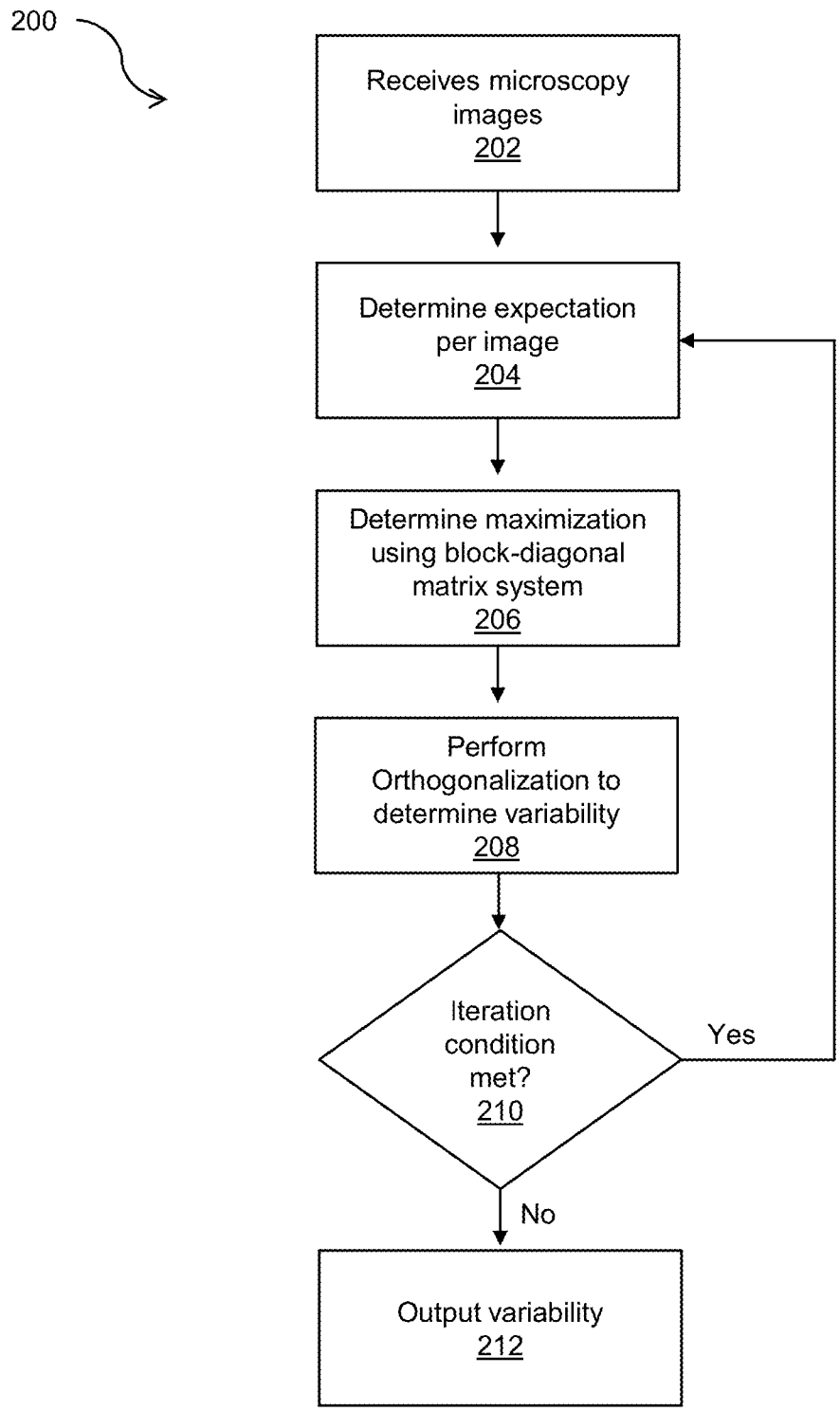
FIG. 3 shows a method for determining variability of cryo-EM protein structures, according to an embodiment.

Turning to FIG. 3, shown is a flowchart for a method 200 for determining variability of cryo-EM protein structures, in accordance with an embodiment.

At block 202, the inputs module 122 receives input images $X_i$, receives poses $\phi_i$, and can, in some cases, receive a 3D density map $V_0$ (hereafter referred to as the consensus reconstruction). The poses, and in some cases the consensus reconstruction, may have been created by any suitable refinement approach that performs a 3D reconstruction of the images. Such suitable refinement approach outputs the poses $\phi_i$ for each image, and in some cases, also outputs a consensus reconstruction. If the inputs module 122 does not receive a consensus reconstruction, it can reconstruct a consensus reconstruction using any suitable approach that performs 3D reconstruction of the images using the received poses.

The system 100 solves for a linear model of variability, $V(z_i)=\Sigma_k z_{ik} V_k$. The system's 100 task is to solve for the $V_k$ and $z_i$ that best fit the data, where $z_i$ are the per-image coordinate values and subscript k is the index of the variability component. "Best fit" in this context means that the system seeks the solution that maximizes the probability of having observed the images $X_i$.

The system 100 can use a generative model as follows:

$$X_i = \alpha C_i P(\phi_i) V(z_i) + \eta$$

$$X = \alpha C P(V_0 + z_1 V_1 + z_2 V_2 + \ldots) + \eta$$

$$X = \alpha C P V_0 + \alpha \sum_k z_k C P V_k + \eta$$

$$X = \alpha Y_0 + \sum_k w_k Y_k + \eta$$

Here X is the received image (referred to as an experimental image), from pose (given by projection P, including shift) with CTF C and overall contrast scale $\alpha$. The noise $\eta$ is noise in each experimental image can be assumed to be Gaussian. The second equation is referring only to a single image i so the i subscripts are dropped for clarity. The overall contrast scale $\alpha$ is absorbed into the definition of $w_k = \alpha z_k$ for the component terms, but is generally required for the base term $Y_0$. Here, $w_k$ are "weighted coordinates" formed by multiplying the coordinates $z_k$ by the contrast scale, and are introduced as a notational and computational convenience. It can be assumed that $V_0$ and P and C are known. Here, $V_0$ is the known 3D density map from a consensus reconstruction, as described herein. In this way, the system 100 is trying to find the maximum likelihood estimates of $V_k$, while dealing with the nuisance variables z. There are also other possible constraints, such as that the $V_k$ are orthogonal and of unit norm. These can be dealt with, but generally do not require constrained optimization as has been used in other approaches. The generative model described above captures the problem of finding variability components and coordinates that explain the heterogeneity in the set of particle images. The generative model itself is an aide to derive the computational operations and implementations necessary to solve the problem.

Accordingly, the overall optimization problem necessary to solve in order to find optimal, or near optimal, fitting values for variability components and coordinates, is:

$$\min_{V,w} E = \sum_i \frac{1}{2} \left\| X_i - \alpha_i Y_{i0} - \sum_k w_{ik} C_i P_i V_k \right\|^2$$

$$\min_{V,w} E = \sum_i \frac{1}{2} \left\| D_i - \sum_k w_{ik} C_i P_i V_k \right\|^2$$

Where $D_i$ is the experimental image minus the $\alpha$-scaled projection of the consensus structure $Y_0$. E is the optimization objective function, which corresponds to the log-probability of observing the images X under the generative model. This log-probability corresponds to the Guassian noise model above. A modified version of this log-probability can also be written for the case where there is a noise model $\sigma^2$ that is colored in real or Fourier space, but this is left out of the equations for clarity, without loss of generality.

The optimization module 124 performs iterative optimization to solve the optimization problem. Iterative optimization of this general type is sometimes known as Expectation-Maximization. At block 204, the optimization module 124 determines expectation (E-step) per single image as:

$$\min_w \frac{1}{2} \left\| D - \sum_k w_k C P V_k \right\|^2$$

$$\frac{d}{dw_j} = 0 = (-CPV_j)^H \left(D - \sum_k w_k CPV_k\right) = (-Y_j)^H D + \sum_k w_k Y_j^H Y_k$$

$$[Y_j^H Y_k]_{jk} [w_k]_k = [Y_j^H D]_j$$

Here, the objective function E is minimized by computing the derivative and setting to zero. The last line of the above equation is a linear system where the matrix is $Y_j^H Y_k$ terms which are inner-products of slices of the various variability component volumes and the right-hand-side is $Y_j^H D$ terms which are inner products of the subtracted data and the variability components. The matrix is symmetric and positive definite (being the hessian of a convex quadratic form). The optimization module 124 solves for the $w_k$, which allows determination of the $z_k$ because $\alpha$ is known for every image. Thus, the optimization module 124 determines the above by solving a single K×K matrix, for each image.

For block 204, the optimization module 124 can also optimize over the per-particle scale factor $\alpha$. This is a single dimension quadratic minimization with closed form solution given by the quadratic formula. In block 204, the optimization module 124 can also perform re-optimization over per-particle pose. The poses are as initially provided in block 202. Re-optimization over poses can be performed using any suitable approach for pose search; for example, local or global discrete sampling searches.

At block 206, the optimization module 124 performs maximization (M-step) optimization across a whole dataset or batch of input images $X_i$ as:

$$\min_V \sum_i \frac{1}{2} \left\| D_i - \sum_k w_{ik} C_i P_i V_k \right\|^2 \text{ s.t. } V_k^T V_j = 0 \; \forall \; j \neq k$$

The above equation describes an optimization problem. Other approaches to solving this or similar optimization problems generally have to make further approximations or assumptions in order to proceed. In contrast, the present embodiments can proceed without any further approximations or introduction of new assumptions.

The optimization module 124 determines the above optimization problem in closed form. First, ignoring the constraints and taking the gradient of the objective function and setting to zero:

$$\min_V \sum_i \frac{1}{2} \left\| D_i - \sum_k w_{ik} C_i P_i V_k \right\|^2 \text{ s.t. } V_k^T V_j = 0 \; \forall \; j \neq k$$

$$\frac{d}{dV_j} = 0 = \sum_i (-w_{ij} C_i P_i)^H \left(D_i - \sum_k w_{ik} C_i P_i V_k\right) =$$

$$\sum_i \left(-w_{ij} P_i^H C_i^H D_i + \sum_k w_{ij} w_{ik} P_i^H C_i^H C_i P_i V_k\right)$$

$$\sum_k \left(\sum_i w_{ij} w_{ik} P_i^H C_i^H C_i P_i\right) V_k = \sum_i w_{ij} P_i^H C_i^H D_i$$

$$\sum_k H_{jk} V_k = h_j$$

The last line of the above equation is a large matrix that could be difficult to solve, especially under the constraints required (where all $V_k$ and $V_j$ are orthogonal for $j \neq k$). The optimization module 124 advantageously handles such a large matrix equation by substantially simplifying it (without approximation) via rearranging it. Furthermore, the constraints are handled in a special way, as described herein. Each matrix $H_{jk}$ is a diagonal matrix, and the complete matrix system in the last line of the above equation above is a very large block-matrix system. In ordinary form, the block-matrix system is a banded-diagonal system. However, by re-arranging the components in the block-matrix system, it can be transformed into a block-diagonal system, where each block is a K×K system corresponding to one particular Fourier coefficient of the volumes $V_k$. Since this block-matrix is block-diagonal, it is separable, and therefore each small K×K system can be solved independently, which makes solving the block-matrix system computationally feasible. Each K×K block-matrix system provides the solution for all K Fourier coefficients that lie in the same 3D location across all the volumes $V_k$.

For further clarity, each $H_{jk}$ matrix is created as the sum of weighted compositions of projection ($P_i$) and back-projection ($P_i^H$) operators. These operators can be defined using interpolation schemes; for example, nearest neighbor interpolation, trilinear interpolation, tricubic interpolation, and the like. In these cases, the $P_i^H P$ product is implemented as a diagonal matrix. Therefore, each $H_{jk}$ is a diagonal matrix. To understand the structure of the problem, the entire set of linear equations defining the M-step above can be written as:

$$\begin{bmatrix} H_{11} & H_{12} & \ldots & H_{1K} \\ H_{21} & H_{22} & \ldots & H_{2K} \\ \vdots & & \ddots & \vdots \\ H_{K1} & H_{K2} & \ldots & H_{KK} \end{bmatrix} \begin{bmatrix} V_1 \\ V_2 \\ \vdots \\ V_K \end{bmatrix} = \begin{bmatrix} h_1 \\ h_1 \\ \vdots \\ h_K \end{bmatrix}$$

In the above, the large matrix on the left is a banded diagonal matrix. The rows and columns of the matrix equation can be reordered without changing the solution of the equation, in order to transform the problem into a block-diagonal problem with many K×K blocks. The first K×K block contains the first diagonal elements of each $H_{jk}$ matrix. The second K×K block contains the second diagonal elements of each $H_{jk}$ matrix, and so on. Each of these blocks can then be solved independently, yielding the full solution to the problem in closed form.

Using the above approach, allows feasibly solving in closed form, within the context of solving the problem of 3D variability. Generally, other approaches have resorted to complex and cumbersome approaches that cannot effectively and feasibly solve the problem and have had to rely on resolving only crude low-resolution results. Advantageously, the approach performed by the optimization module 124 is able to recover high-resolution 3D variability components, able to treat large numbers of images from many viewing directions, and able to correctly deal with the CTF of the microscope.

Using the creation of the block-diagonal matrix system allows for effective solution of the M-step reconstruction problem accurately and efficiently without having to resort to approximate approaches or ignoring parts of the problem. Thus, the system 100 is, for example, able to resolve flexible protein motion at high resolutions.

Other approaches have attempted to solve the M-step optimization while enforcing the constraint that each of the $V_k$ components must be orthogonal. This is a constraint that must be applied in order to obtain multiple different independent components of variability. The present inventors determined that this constraint can be applied after solving the matrix problem above, without constraints, and yields an accurate and effective result. Advantageously, the system 100 can use orthogonalization operations iteratively during optimization to correct non-orthogonal results, rather than trying to directly enforce the orthogonality constraint throughout. This "relaxation" allows performance and does not negatively affect the results.

At block 208, the optimization module 124 solves the matrix equation directly without constraints, by solving all the requisite K×K systems. This yields solutions for $V_k$ which are not orthogonal but span the linear subspace of the true components of variability. Orthogonalizing these $V_k$ can be performed by the optimization module 124 by determining a cross-correlation matrix of the $V_k$, diagonalizing the K×K matrix using eigendecomposition, and then using the resulting rotation matrix to "rotate" the $V_k$ density vectors so that they become orthogonal (or in other cases, orthonormal). Solving of the matrix equation can be performed immediately after solving the M-step matrix equation described above, in each iteration of E-M. The orthogonalization operation can be defined as $$Q_{jk} = V_j^T V_k$$

$$R\Lambda R^T = Q$$

-continued
$$[V_1' V_2' \ldots V_K'] = [V_1 V_2 \ldots V_K] R \Lambda^{-1/2}$$

where the $V'_k$ results are the orthogonalized components of variability. These resulting $V'_k$ vectors describe a component of variability each, but note that after applying this orthogonalization operation, the $w_k$'s that were used in the M-step no longer correctly correspond as coordinates of a linear combination of these $V'_k$ vectors. Instead, an additional E-step must be computed to retrieve correct $w_k$'s and therefore $z_k$.

In other cases, instead of eigendecomposition-based orthogonalization, the orthogonalization module 124 performs a sequential technique (known as Gram-Schmidt orthogonalization) that can be used to orthogonalize the $V_k$. In Gram-Schmidt orthogonalization, an orthogonal basis for the subspace spanned by $V_k$ is created one basis vector at a time, with the benefit that orthogonalization of the $V_k$ in this manner is more stable from iteration to iteration.

In the M-step, in some cases, along with solving for updated $V_k$ terms, it is also possible to update the estimate of noise variance, $\sigma^2$. This is performed by a batch optimization across the whole dataset, and the solution is a closed form computation of the per-wavelength residual power of the image data after subtracting the projection given by the generative model.

In most cases, blocks 204 to 208 can be iterated multiple times, with the first iteration initialized with random values for the $z_i$ coordinates. After several iterations, the $V_k$ and $z_i$ will generally converge to yield components of 3D variability. Each iteration involves applying the solutions to the E-step and M-step sub-problems described above. Each iteration uses the outputs of the previous iteration to iteratively optimize the overall optimization problem in order to find the best-fitting variability components. At block 210, the optimization module 124 can determine if a condition for continuing iterations has been met; such condition can be based on, for example, a predetermined number of iterations or determining if convergence can be detected based on the change in the values from one iteration to the next (such as where the change is zero or below a predetermined threshold). In some cases, in each iteration, it is also possible to apply both a real-space and Fourier-space mask to the $V_k$. The real-space mask can be a 3D map of values between zero and one, with values of zero indicating a region to be ignored and a value greater than zero indicating a region to be retained during optimization. The mask is applied by directly multiplying each value in each variability component with the corresponding mask value. Similarly, the Fourier-space mask can be a 3D Fourier-space map of values between zero and one, with values of zero indicating a spatial frequency to ignore. This makes it possible to enforce a limitation in terms of which part of a protein to examine (real-space) and/or at what resolution to look for variability (Fourier space). In some cases, symmetry of the $V_k$ can also be enforced.

At block 212, the output module 126 outputs the variability of the cryo-EM protein structures.

While method 200 generally refers to 2D data to generate 3D variability components, it is understood that it can likewise be applied to 2D data to generate 2D variability components and it can be applied to 3D data to generate 3D variability components.

Method 200 can be used for determining the components of variability of a molecule. In some cases, the output module 126 can output a visualization of these components by showing the volume $V(z_k)$ as a function of the coordinates z. Advantageously, visualization can provide significant insight into the function of a biomolecule, but there are other applications of the method 200.

The method 200 determines components of variability. In some cases, considering the set of possible molecules $V(z_k)$ as a probability distribution, the components of variability are the leading eigenvectors of the covariance. Equivalently, they are the directions in the space of 3D structures in which there is maximum variability. When $V(z_k)$ consists of two or more discrete clusters, the top components of variability will span the subspace containing the cluster centers (under some conditions, such as that the distance between clusters is sufficient). This means that the components of variability can actually be used as a direct means by which to distinguish clusters. In fact, the amount of variability and presence of clusters can be automatically identified using the $z_i$ values. Additionally, the number of distinct clusters can be identified automatically. Both the presence of clusters and the number of clusters can be determined using any suitable clustering approach; for example, Gaussian Mixture Models, K-Means clustering, Spectral clustering, DBSCAN, or the like.

Further, the notion of clustering by identifying variability can be used hierarchically, both for 2D and 3D classification. A given cluster of particles can be used to determine the components of variability using the embodiments described herein. Then, subclusters can be detected using any suitable clustering approach applied to the z values computed by the system 100. Each subcluster can be separated based on the z values, and then sub-classified into sub-sub-clusters in the same way. This can be repeated until remaining clusters have no substantial variability remaining.

In some cases, the components of variability can be used as a starting point to perform fully flexible refinement of a 3D structure. Components that describe flexibility will have a continuous spread of $z_i$ values. Using the component itself, which is a linear model of variability, a non-linear model of variability can be fit. This non-linear model can be a model that represents the molecule as a source 3D density $V_0$ that is transformed by a "flex" mapping T so that $V=T(V_0,z_i)$. The flex mapping is a function that "bends" the density $V_0$ by various amounts in various directions depending on $z_i$. Once the model T is fit to the linear components of variability, the density $V_0$ can be refined through the flexible mapping, by, for example, considering the 3D structure to be made up of multiple small rigid parts that move together along the flexible mapping. Reconstructing the density $V_0$ in this way can yield an improved 3D resolution and structure quality, along with insight into the flexible motion of the molecule. The flex model T can also be improved iteratively.

In embodiments of the present disclosure, the 3D pose $\phi_i$ of each observed image $X_i$ can be assumed to be known and fixed. In some cases, this may not be necessary because it may be possible to re-align the poses iteratively after solving for the components and the coordinates. In such cases, each image $X_i$ is aligned to the reference $V(z_i)$ rather than to the initial consensus reference $V_0$. This allows for the scenario where the initial poses are incorrect by some margin, but after solving for the components of variability, the poses can be corrected based on the variability present. For example, with membrane proteins, the micelle surrounding the membrane domain of the protein often has significant variability. By identifying this variability and accounting for it during 3D alignment, the poses can be improved. This re-optimization of poses can be carried out as described in block 204.

Figure 4:
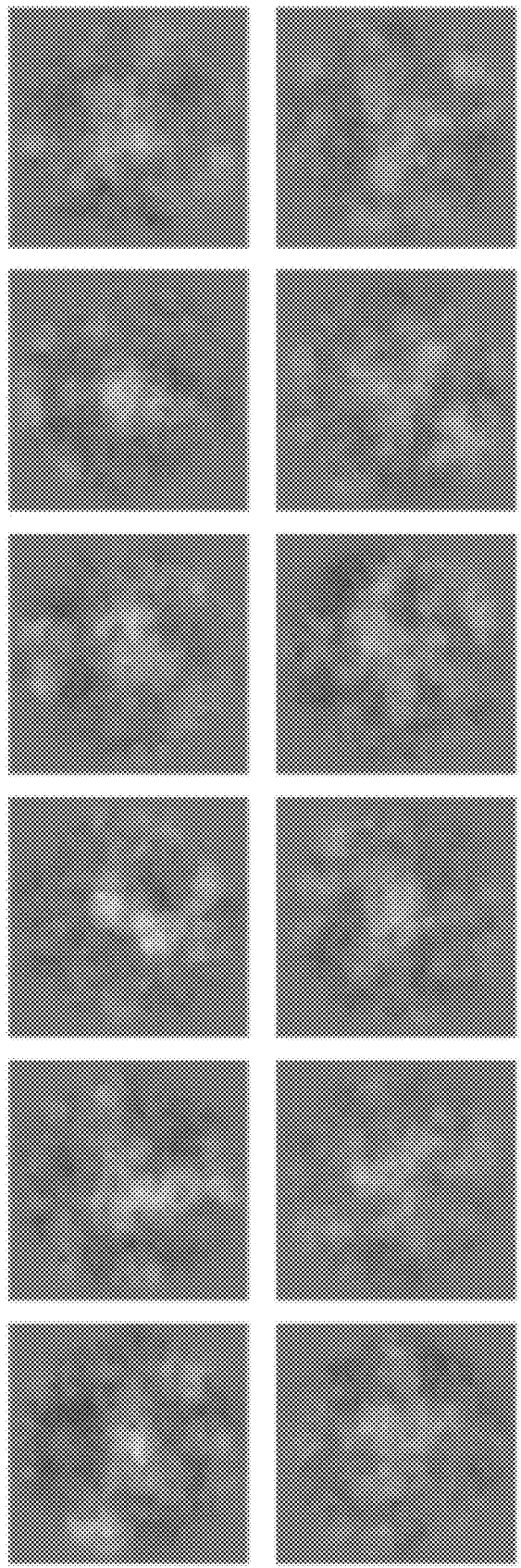
FIG. 4 illustrates examples of single particle experimental images.
Figure 5:
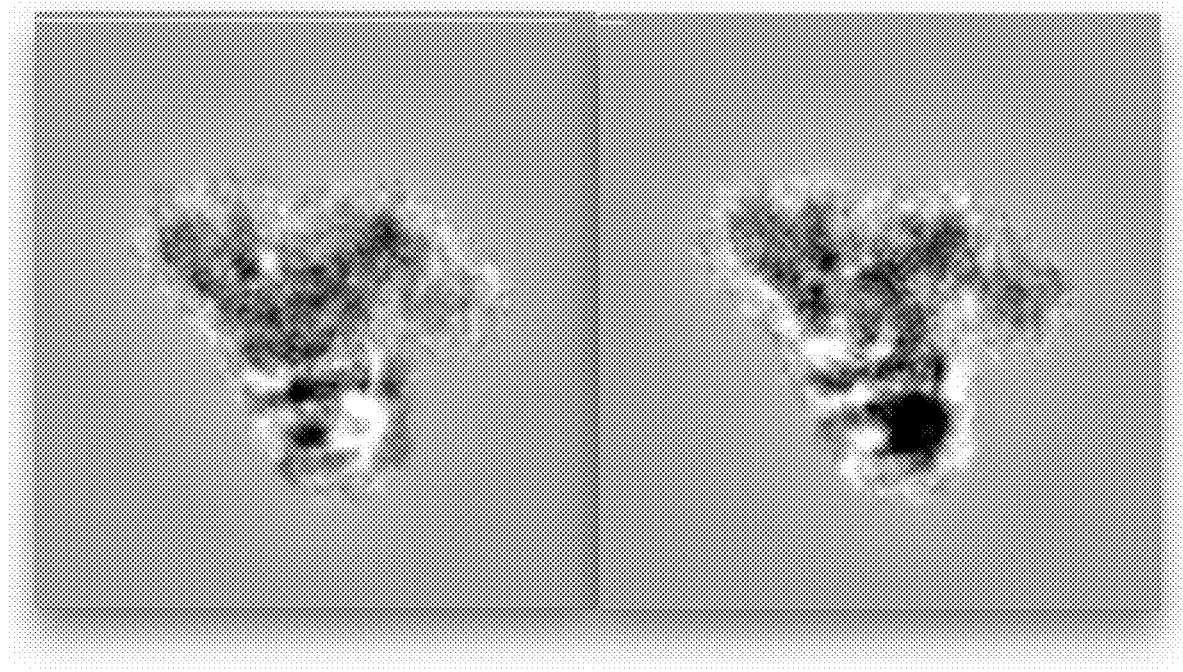
FIG. 5 illustrates an example result of applying the method of FIG. 3 to snRNP data from FIG. 4 to determine 2D components of variability.

The present inventors conducted example experiments to evaluate the advantages of the present embodiments. FIG. 4 illustrates examples of single particle 2D experimental images, $X_i$. Each image contains one protein particle in a particular 3D pose $\phi_i$ and a particular conformational state. In this case, the particle images are of a spliceosome protein called snRNP. FIG. 5 illustrates an example result of applying the method 200 to the snRNP data from FIG. 4 to determine 2D components of variability. The left image shows the protein molecule in a state where the flexible domain (bottom) is bent to the left, while the right image shows the state where the flexible domain is bent to the right. In this case, a range of intermediate images can also be determined that show the motion of the parts.

Figure 6:
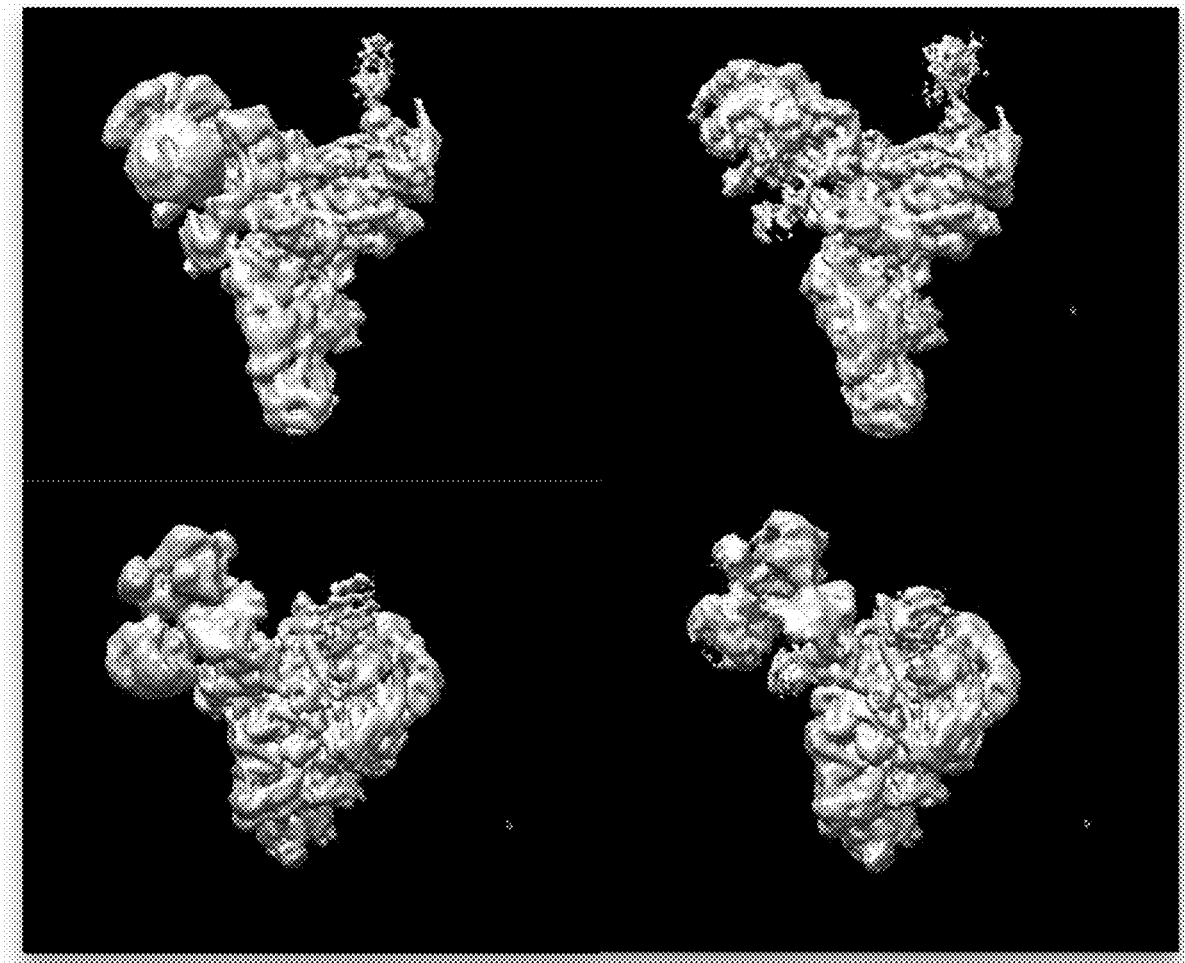
FIG. 6 illustrates an example result of applying the method of FIG. 3 to the snRNP data from FIG. 4 to determine 3D components of variability.

FIG. 6 illustrates an example result of applying the method 200 to the snRNP data to determine 3D components of variability. The top-left image shows a front view, with flexible domain down. The top-right image shows a front view, with flexible domain up. The bottom-left image shows a side view, with flexible domain forward. The bottom-right image shows a side view with flexible domain back. In this case, a range of intermediate states can be also determined.

Figure 7:
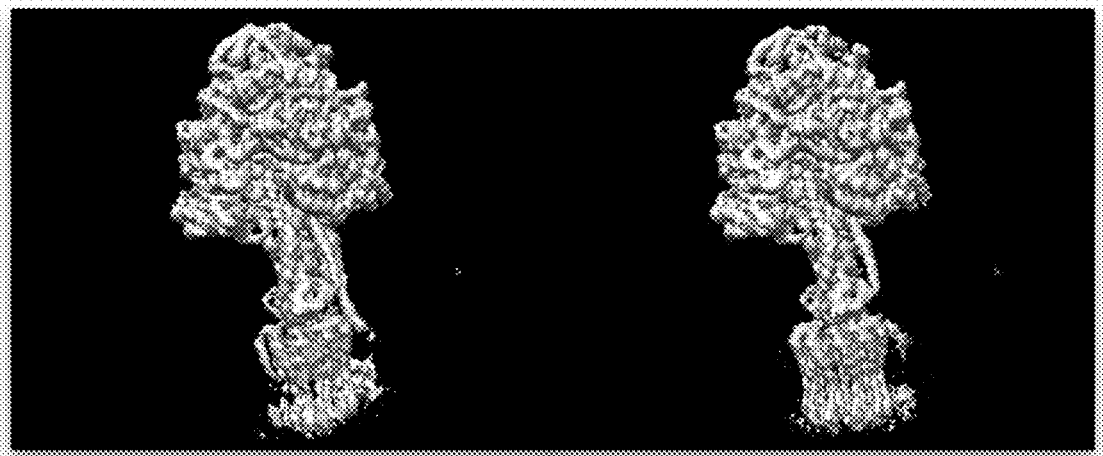
FIG. 7 illustrates an example of high-resolution flexibility determined with the method of FIG. 3.

FIG. 7 illustrates an example of high-resolution flexibility determined with the method 200. The left image shows an ATPase molecule with central stalk bent to the right. The right image shows a state where central stalk is bent to the left. In this case, a range of intermediate states can be also determined. This high-resolution result retains information about the position of helices and even their pitch within the structure, but also shows the motion of the flexible stalk.

Figure 8:
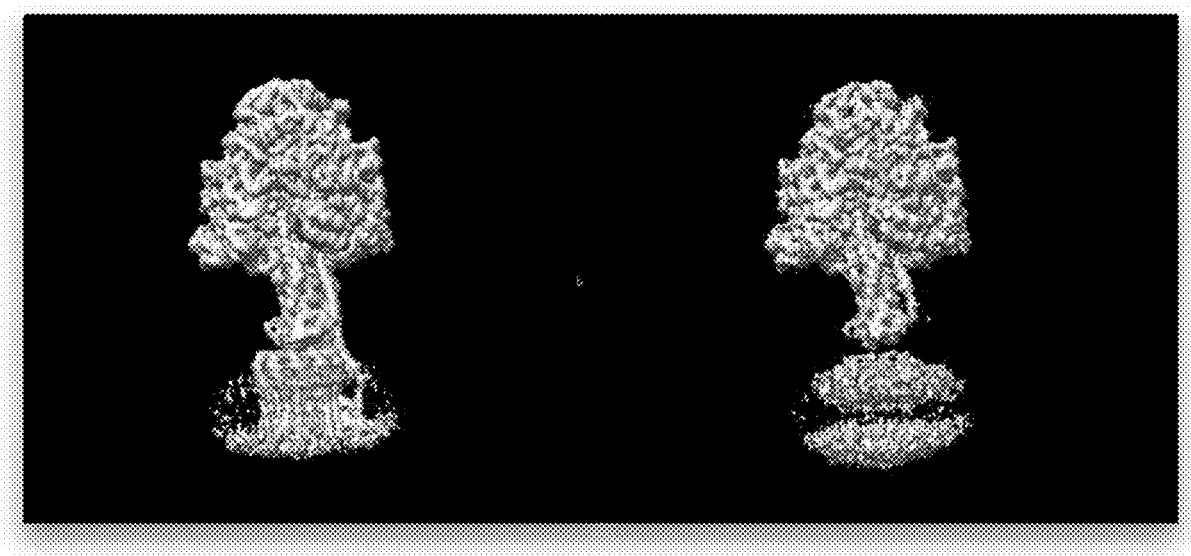
FIG. 8 illustrates an example of a second component of variability from the same dataset as FIG. 7.

FIG. 8 illustrates an example of a second component of variability from the same ATPase dataset as FIG. 7. In this case, the component shows the clear dissociation and loss of the transmembrane domain of the protein. This is an example of the variability determination being useful for finding discrete conformational states.

Figure 9:
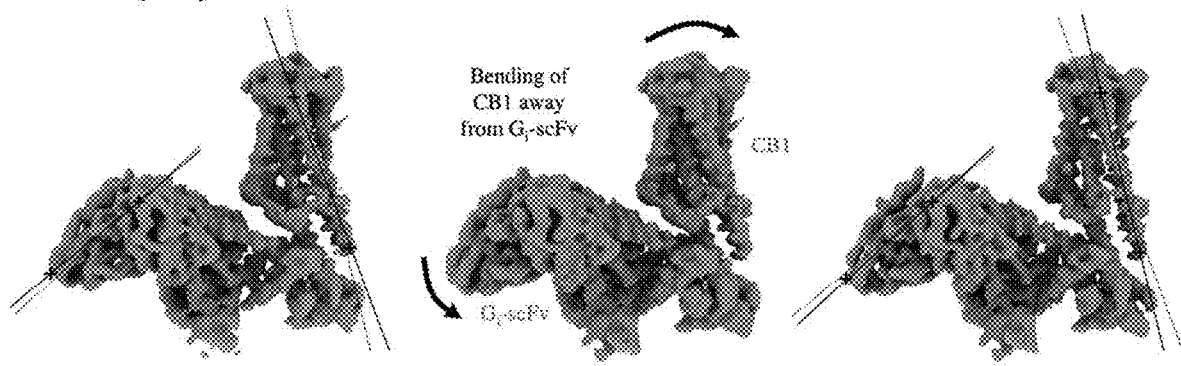
FIG. 9 illustrates an example of results of 3D variability analysis of the method of FIG. 3 with three variability components on G protein-coupled receptor (GPCR) protein data.
Figure 9:
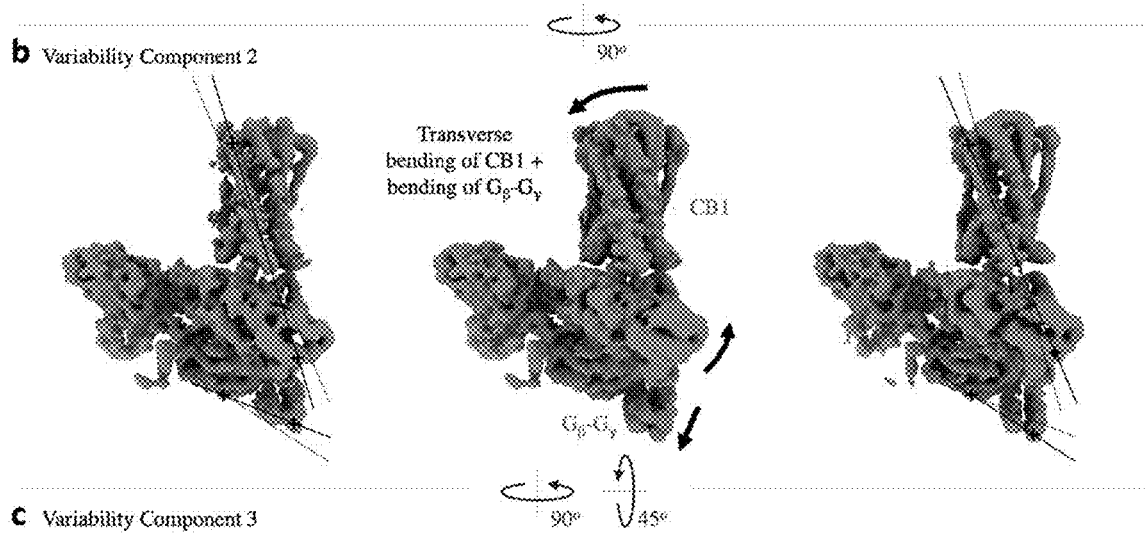
Figure 9:
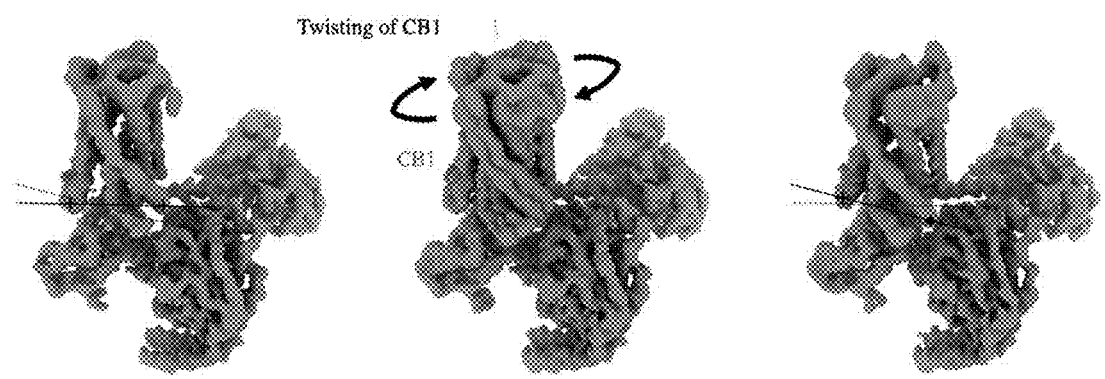

FIG. 9 illustrates an example of results of 3D variability analysis with three variability components on 250,649 particle images of a Cannabinoid Receptor1-G GPCR complex. This result demonstrates the capacity for 3D variability analysis to resolve detailed high resolution motion of small proteins and small subregions of proteins. The top row of the image illustrates that component 1 resolves bending of the CB1 transmembrane region away/towards the G-protein. Bending also affects the pose of the scFv subunit. The middle row of the image illustrates that component 2 resolves a perpendicular (compared to component 1) bending of the CB1 region, with simultaneous motion of the G-G pair of helices. The bottom row of the image illustrates that component 3 resolves twisting of the CB1 transmembrane domain around an axis perpendicular to the membrane. This experimental result is significant because it shows that unlike other approaches, the 3D variability analysis of method 200 has the ability to resolve small detailed flexible motions of parts of a very small protein molecule. Other approaches generally only work on larger proteins and with coarse motion. Thus, the 3D variability analysis of method 200 dramatically improves the amount of biologically insightful information that can be extracted from single particle cryo-EM data.

Figure 10:
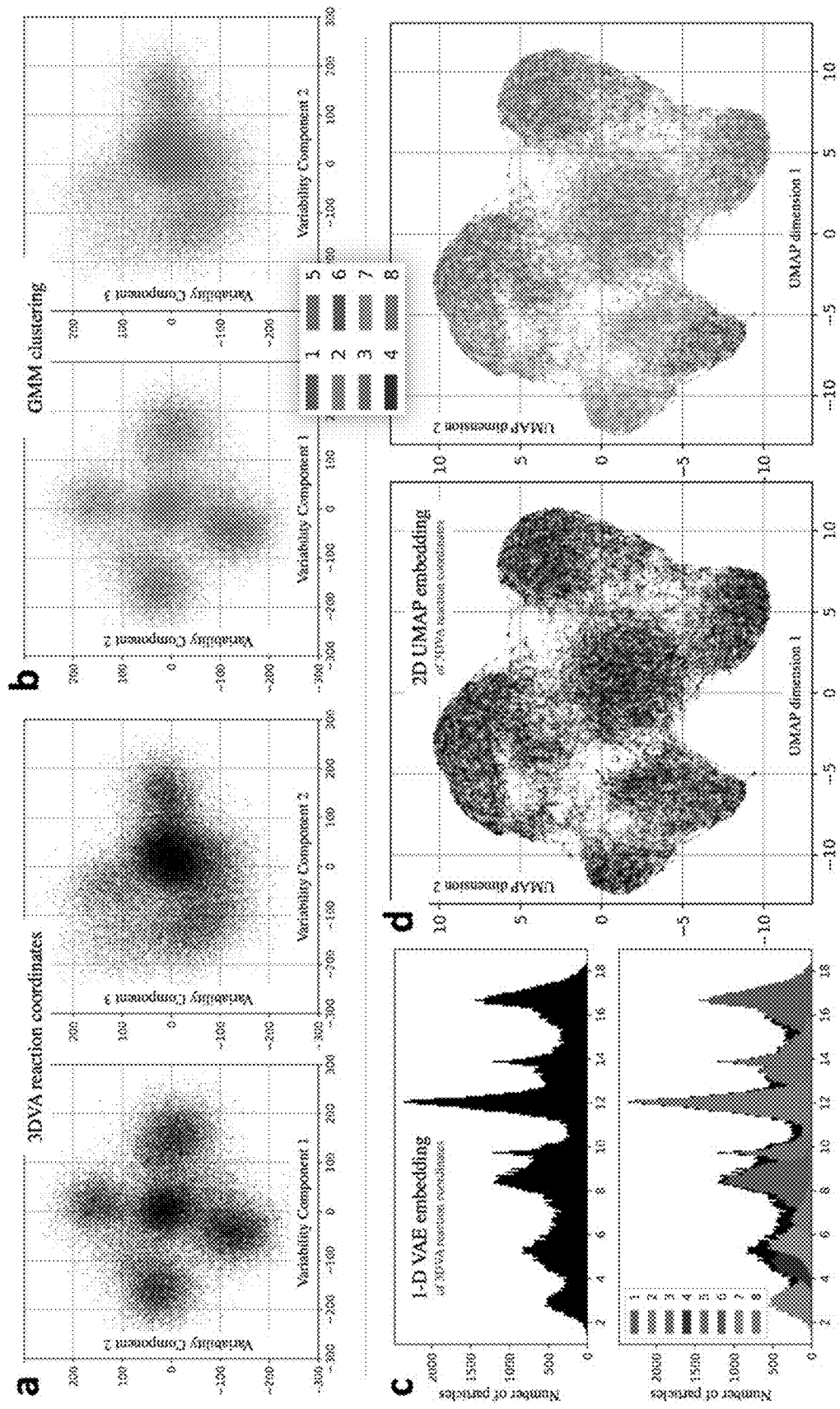
FIGS. 10 and 11 illustrate charts showing example of experimental results of 3D variability analysis of the method of FIG. 3 with four components on 131,899 particle images of a bacterial ribosomal large subunit.
Figure 11:
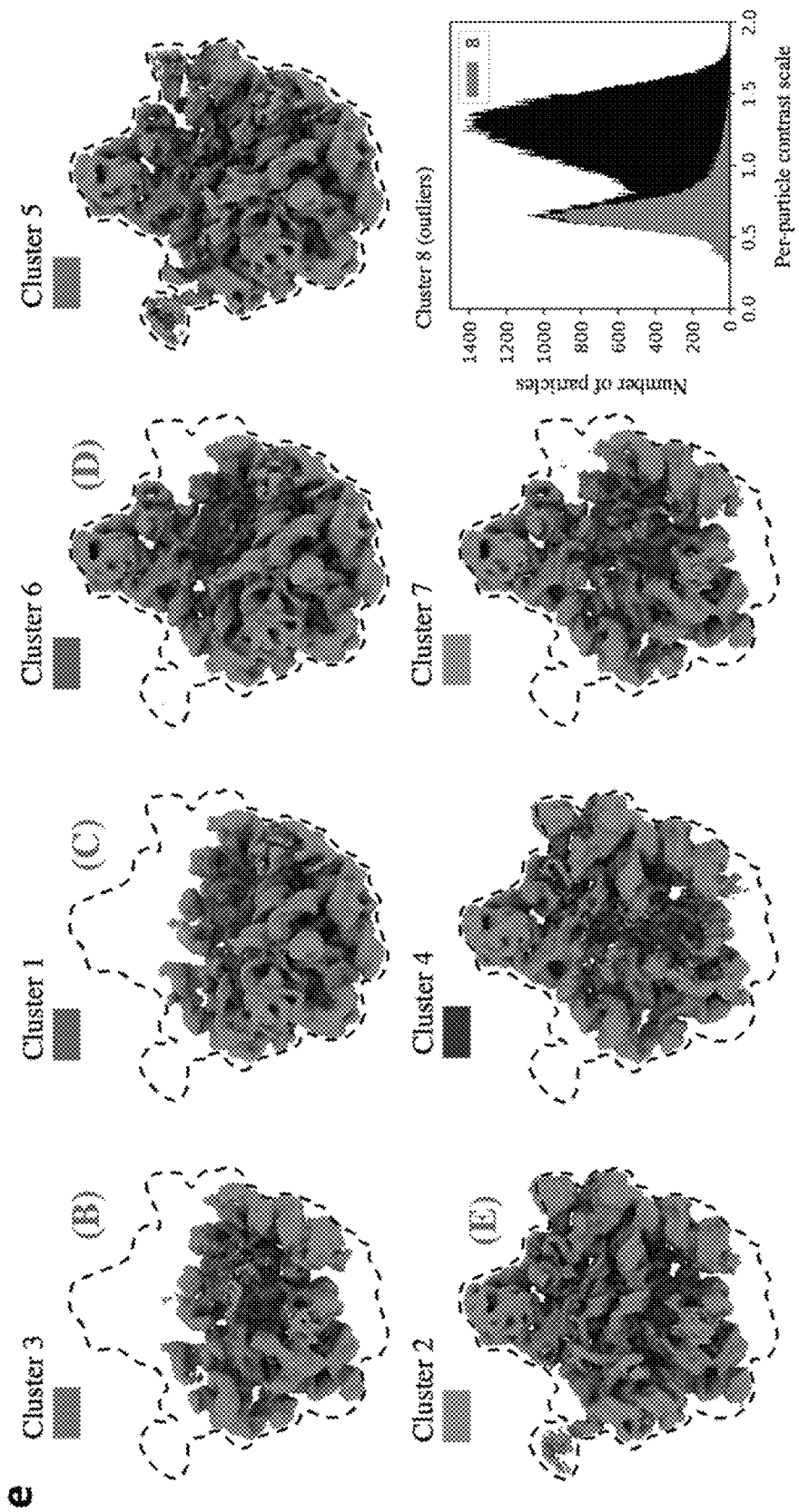

FIGS. 10 and 11 illustrate an example of the experimental results of 3D variability analysis (3 DVA) of method 200 with four components on 131,899 particle images of a bacterial ribosomal large subunit. The 3D variability analysis identifies clusters corresponding to discrete conformational states. The top-left charts (a) of FIG. 10 illustrate example 3 DVA particle reaction coordinates, as 2D scatter plots of sequential pairs of dimensions. The top-right charts (b) of FIG. 10 illustrate example reaction coordinates organized by 8-way Gaussian Mixture Model (GMM) clustering. The bottom-left charts (c) of FIG. 10 illustrate example 1D histogram of Variational Autoencoder (VAE) embedding of reaction coordinates. The histogram shows seven major peaks. Overlaid histograms of each of the GMM clusters show that peaks correspond to clusters. The bottom-right charts (d) of FIG. 10 illustrate example 2D Uniform Manifold Approximation and Projection (UMAP) embedding of reaction coordinates, showing overall geometry of clusters. FIG. 11 illustrates example 3D reconstructions from particles in each GMM cluster. Cluster 3 contains the least assembled complex, and other clusters have more subunits assembled. The 8th cluster contains outliers for which 3D DVA estimates lower per-particle scale factor α (histogram). This experimental result shows that 3D variability analysis of method 200 is capable of detecting nuanced discrete conformational heterogeneity directly from single particle cryo-EM data. This result substantially improves the biological insight that can be extracted from the data. The above use of the VAE and UMAP embeddings can be used to help visualize the results of the 3D variability analysis of method 200.

Although the invention has been described with reference to certain specific embodiments, various modifications thereof will be apparent to those skilled in the art without departing from the spirit and scope of the invention as outlined in the claims appended hereto. The entire disclosures of all references recited above are incorporated herein by reference.

The invention claimed is:

1. A method for determining variability of cryo-EM protein structures from a set of cryo-electron microscope images, the variability represented as a model comprising variability components in a weighted sum, the weights in the weighted sum comprising variability coordinates for each component for each image, the method comprising:
   receiving the set of images;
   performing iterative optimization to determine updated variability components and updated variability coordinates for the received set of images, each optimization iteration comprising:
      determining the updated variability coordinates for individual images from the set of images using a current value of the variability components; and
      determining the updated variability components for multiple images of the set of images, using the updated value of the variability coordinates, by solving a set of linear equations, the linear equations comprising a sum of weighted compositions of projection and back-projection operators, the equations are solved by arranging the equations into a block-diagonal matrix form; and
   outputting the variability components.

2. The method of claim 1, wherein determining the updated variability coordinates comprises solving a linear system, the linear system comprising inner-products between projections from multiple variability components and inner-products between image data of the set of images and variability components.

3. The method of claim 1, wherein the optimization iteration further comprising determining a per-particle contrast scale factor, the per-particle contrast scale factor is multiplied on the weighted sum of variability components in the model.

4. The method of claim 1, wherein the block-diagonal form is solved by separating the block-diagonal into independent sub matrices.

5. The method of claim 1, wherein the iterations are initialized with a random initial value for the unknown variability coordinates.

6. The method of claim 1, wherein the iterations are performed a predetermined number of times.

7. The method of claim 1, wherein the iterations are performed until convergence is detected based on a change in values for variability between successive iterations.

8. The method of claim 1, further comprising performing orthogonalization of the variability components after solving the set of linear equations, and wherein orthogonalization of the variability components comprises determining a cross-correlation matrix of the variability components, diagonalizing the cross-correlation matrix using eigendecomposition, and using a resulting rotation matrix on density vectors of the variability components to become orthogonal.

9. The method of claim 8, wherein orthogonalization of the variability components comprises performing Gram-Schmidt orthogonalization.

10. The method of claim 1, further comprising clustering the set of images into separate subsets associated with different conformations of the protein structure using the optimized variability coordinate values as input.

11. The method of claim 10, further comprising performing the iterative optimization on the subsets of images, and further comprising performing clustering of the optimized variability coordinate values on the subsets of images.

12. A system for determining variability of cryo-EM protein structures from a set of cryo-electron microscope images, the variability represented as a model comprising variability components in a weighted sum, the weights in the weighted sum comprising variability coordinates for each component for each image, the system comprising one or more processors in communication with a memory storage, the one or more processors configured to execute:
   an inputs module to receive the set of images;
   an optimization module to perform iterative optimization to determine updated variability components and updated variability coordinates for the received set of images, each optimization iteration comprising:
      determining the updated variability coordinates for individual images from the set of images using a current value of the variability components; and
      determining the updated variability components for multiple images of the set of images, using the updated value of the variability components, by solving a set of linear equations, the linear equations comprising a sum of weighted compositions of projection and back-projection operators, the equations are solved by arranging the equations into a block-diagonal matrix form; and
   an output module to output the variability components.

13. The system of claim 12, wherein determining the updated variability coordinates comprises solving a linear system, the linear system comprising inner-products between projections from multiple variability components and inner-products between image data of the set of images and variability components.

14. The system of claim 12, wherein the optimization iteration further comprising determining a per-particle contrast scale factor, the per-particle contrast scale factor is multiplied on the weighted sum of variability components in the model.

15. The system of claim 12, wherein the block-diagonal form is solved by separating the block-diagonal into independent sub matrices.

16. The system of claim 12, wherein each iteration comprises a random initial value for the unknown coordinates.

17. The system of claim 12, wherein the iterations are initialized with a random initial value for the unknown variability coordinates.

18. The system of claim 12, wherein the optimization module further performs orthogonalization of the variability components after solving for the set of linear equations, and wherein determining the orthogonalization of the variability components comprises performing Gram-Schmidt orthogonalization.

19. The system of claim 12, wherein the optimization module further clusters the set of images into separate subsets associated with different conformations of the protein structure using the optimized variability coordinate values as input.

20. The system of claim 19, wherein the optimization module further performs the iterative optimization on the subsets of images, and further performs clustering of the optimized variability coordinate values on the subsets of images.

* * * * *